United States Patent
McDevitt et al.

[11] Patent Number: 5,935,129
[45] Date of Patent: Aug. 10, 1999

[54] METHODS AND APPARATUS FOR ANCHORING OBJECTS TO BONE

[75] Inventors: Dennis McDevitt, Upton; John Rice, Lincoln; Mark A. Johanson, Littleton, all of Mass.

[73] Assignee: Innovasive Devices, Inc., Marlborough, Mass.

[21] Appl. No.: 08/813,914

[22] Filed: Mar. 7, 1997

[51] Int. Cl.⁶ ................................................. A61B 17/56
[52] U.S. Cl. ............................................. 606/72; 606/232
[58] Field of Search ............................ 606/72, 73, 88, 606/96, 86, 232

[56] References Cited

U.S. PATENT DOCUMENTS

| | | |
|---|---|---|
| Re. 34,293 | 6/1993 | Goble et al. . |
| 2,381,050 | 8/1945 | Hardinge . |
| 3,036,482 | 5/1962 | Kenworthy et al. . |
| 3,566,739 | 3/1971 | Lebar . |
| 3,708,883 | 1/1973 | Flander . |
| 3,842,824 | 10/1974 | Neufeld . |
| 4,013,071 | 3/1977 | Rosenberg . |
| 4,091,806 | 5/1978 | Aginsky . |
| 4,140,111 | 2/1979 | Morrill . |
| 4,408,938 | 10/1983 | Maguire . |
| 4,484,570 | 11/1984 | Sutter . |
| 4,492,226 | 1/1985 | Belykh et al. . |
| 4,506,670 | 3/1985 | Crossley . |
| 4,590,928 | 5/1986 | Hunt et al. . |
| 4,632,100 | 12/1986 | Somers et al. . |
| 4,708,132 | 11/1987 | Silvestrini . |
| 4,716,893 | 1/1988 | Fischer et al. . |
| 4,741,330 | 5/1988 | Hayhurst . |
| 4,778,468 | 10/1988 | Hunt et al. . |
| 4,834,752 | 5/1989 | Van Kampen . |
| 4,870,957 | 10/1989 | Goble . |
| 4,871,289 | 10/1989 | Choiniere . |
| 4,873,976 | 10/1989 | Schreiber . |
| 4,927,421 | 5/1990 | Goble . |
| 4,940,467 | 7/1990 | Tronzo . |
| 4,944,742 | 7/1990 | Clemow et al. . |

(List continued on next page.)

FOREIGN PATENT DOCUMENTS

| | | |
|---|---|---|
| 0 124 489 | 11/1984 | European Pat. Off. . |
| 0 232 049 | 8/1987 | European Pat. Off. . |
| 0 241 240 | 10/1987 | European Pat. Off. . |
| 0 260 970 | 3/1988 | European Pat. Off. . |
| 0 270 704 | 6/1988 | European Pat. Off. . |
| 0 251 583 | 7/1988 | European Pat. Off. . |
| 0 574 707 | 12/1993 | European Pat. Off. . |
| 0 611 557 | 8/1994 | European Pat. Off. . |
| 2 084 468 | 4/1982 | United Kingdom . |

(List continued on next page.)

*Primary Examiner*—Guy V. Tucker
*Attorney, Agent, or Firm*—Choate, Hall & Stewart

[57] ABSTRACT

The invention provides anchoring devices and methods for coupling an object, such as a suture or soft tissue, to bone. In one aspect of the invention, a bone anchor is placed into compression fit with a predrilled bone hole by pulling an insertion stem at least partially into an anchoring element. In its non-expanded state, the anchoring element is slidably mounted on the proximal end of the insertion stem. The anchoring element has an axial channel at least a portion of which has an inner diameter (or cross-section) smaller than an outer diameter (or cross-section) of at least one portion of the insertion stem. As that larger portion of the insertion stem is pulled through the channel, it causes the walls of the anchoring element to expand outwardly and, thereby, to engage the bone hole walls in a pressure or compression fit. In another aspect of the invention, the larger portion of the insertion stem is a separate component, referred to as an "expander element," that is slidably mounted on the insertion stem distal to the anchoring element. As the insertion stem moves proximally, the expander element is pulled through the channel, causing the walls of the anchoring element to expand into the bone hole walls. A flange, such as a reverse taper, at the distal end of the expander element prevents it from being drawn too far through the anchoring element.

38 Claims, 8 Drawing Sheets

U.S. PATENT DOCUMENTS

| | | |
|---|---|---|
| 4,988,351 | 1/1991 | Poulos . |
| 5,013,316 | 5/1991 | Goble et al. . |
| 5,037,422 | 8/1991 | Hayhurst et al. . |
| 5,046,513 | 9/1991 | Gatturna et al. . |
| 5,084,050 | 1/1992 | Draenert . |
| 5,116,337 | 5/1992 | Johnson . |
| 5,141,373 | 8/1992 | Kendall . |
| 5,141,520 | 8/1992 | Goble et al. . |
| 5,152,763 | 10/1992 | Johnson . |
| 5,169,400 | 12/1992 | Murling . |
| 5,176,682 | 1/1993 | Chow . |
| 5,207,679 | 5/1993 | Li . |
| 5,209,753 | 5/1993 | Biedermann et al. . |
| 5,224,946 | 7/1993 | Hyhurst et al. . |
| 5,236,445 | 8/1993 | Hayhurst et al. . |
| 5,248,231 | 9/1993 | Denham et al. . |
| 5,257,637 | 11/1993 | Gazayerli . |
| 5,258,015 | 11/1993 | Li et al. . |
| 5,268,001 | 12/1993 | Nicholson et al. . |
| 5,324,308 | 6/1994 | Pierce . |
| 5,326,205 | 7/1994 | Anspach, Jr. et al. . |
| 5,354,298 | 10/1994 | Lee et al. . |
| 5,411,523 | 5/1995 | Goble . |
| 5,417,712 | 5/1995 | Whittaker et al. . |
| 5,458,601 | 10/1995 | Young, Jr. et al. . |
| 5,464,427 | 11/1995 | Curtis et al. . |
| 5,472,452 | 12/1995 | Trott . |
| 5,480,403 | 1/1996 | Lee et al. . |
| 5,486,197 | 1/1996 | Le et al. . |
| 5,489,210 | 2/1996 | Hanosh . |
| 5,496,326 | 3/1996 | Johnson . |
| 5,501,683 | 3/1996 | Trott . |
| 5,501,695 | 3/1996 | Anspach et al. . |
| 5,522,845 | 6/1996 | Wenstrom, Jr. . |
| 5,545,180 | 8/1996 | Le et al. . |
| 5,571,104 | 11/1996 | Li . |

FOREIGN PATENT DOCUMENTS

| | | |
|---|---|---|
| WO 88/09157 | 12/1988 | WIPO . |
| WO 89/01767 | 3/1989 | WIPO . |
| WO 92/04874 | 4/1992 | WIPO . |
| WO 95/02998 | 2/1995 | WIPO . |
| WO 95/15726 | 6/1995 | WIPO . |
| WO 95/29636 | 11/1995 | WIPO . |

METHODS AND APPARATUS FOR ANCHORING OBJECTS TO BONE

BACKGROUND OF THE INVENTION

This invention pertains to surgical systems and, more particularly, apparatus and methods for attaching sutures and soft tissue to bone. The invention has application in, for example, the reattachment of tendons and ligaments to bones, such as in procedures to repair anterior cruciate ligaments or to repair torn rotator cuffs.

It is not uncommon for tendons and other soft tissues to tear or to detach from bone. One injury common to athletes, for example, is a "rotator cuff" tear, in which the supraspinatus tendon separates from the humerus, causing pain and loss of ability to elevate and externally rotate the arm. Another common injury is an anterior cruciate ligament (ACL) tear, in which one of the ligaments connecting the femur and the tibia is ruptured. Surgeons are routinely called upon to reattach tendons and other soft tissues to bone in remedying these and other injuries.

One difficulty of such surgery is anchoring tissues or sutures to bone in a manner capable of withstanding the normal stresses of movement. An early procedure, which is still in use, involves sewing the tissue directly to bone by passing a suture through a hole in the bone. This method presents the risk of bore hole migration, i.e., migration of the suture through the sides and edges of the bone hole, especially when used in the weaker bone of older patients.

Metal screws, pins, staples, and other such "anchors" provide an alternative means for affixing soft tissue to bone. While metal offers strong holding ability, especially in hard bone, its use has associated disadvantages including corrosion, metal sensitivity in the patient, and interference with sophisticated imaging techniques such as magnetic resonance imaging. Moreover, the substantial force required to drive metal anchors into bone may cause additional damage.

Many of the problems associated with metal can be mitigated by the use of plastic or bioabsorbable anchors. However, non-metallic anchors typically do not possess the holding power of metal and may also be more fragile.

Among the prior art non-metallic anchors is Hayhurst, U.S. Pat. No. 4,741,330, which describes a suture anchor having a generally bullet-shaped resilient plastic member having a rounded convex base from which wings extend. The wings, which are provided with outward-pointing barbs on their outer surface, diverge radially outward when the member is in a relaxed state. The member is compressed and inserted into a predrilled bone hole, then allowed to relax so that its resilience splays the wings outward against the bone wall. The anchor is set by applying tension to the suture, causing the edges of the wings and the surface barbs to dig into the bone. The anchor is marketed by Acufex Microsurgical and commonly referred to as the "wedge."

An object of the present invention is to provide improve methods and apparatus for anchoring objects, such as sutures, tendons, and soft tissues, to bone.

Another object of the present invention is to provide a bone anchor of simple design and construction.

Another object of the present invention is to provide a bone anchor design suitable for use with a range of biocompatible materials, including metals, plastics and bioabsorbables.

Another object of the present invention is to provide methods and apparatus for anchoring objects to bone which require substantially no impact or impulse required in the emplacement process.

SUMMARY OF THE INVENTION

The above objects are those met by the invention, which provides an anchoring device and methods for coupling an object, such as a suture or soft tissue, to bone. In one aspect of the invention, a bone anchor is placed into compression fit with a predrilled bone hole by pulling an insertion stem at least partially into an anchoring element. In its non-expanded state, the anchoring element is slidably mounted on the proximal end of the insertion stem. The anchoring element has an axial channel at least a portion of which has an inner diameter (or cross-section) smaller than an outer diameter (or cross-section) of at least one portion of the insertion stem. As that larger portion of the insertion stem is pulled through the channel, it causes the walls of the anchoring element to expand outwardly and, thereby, to engage the bone hole walls in a pressure or compression fit.

In a related aspect of the invention, the larger portion of the insertion stem is a separate component, referred to as an "expander element," that is slidably mounted on the insertion stem distal to the anchoring element. As the insertion stem moves proximally, the expander element is pulled through the channel, causing the walls of the anchoring element to expand into the bone hole walls. A flange, such as a reverse taper, at the distal end of the expander element prevents it from being drawn too far through the anchoring element.

In another aspect of the invention, the holding power of the bone anchor is augmented by adding a second anchoring element. The second anchoring element is located between the distal end of the insertion element and the distal end of the first anchoring element. Proximal movement of the insertion stem causes not only the first anchoring element to expand into the bone hole wall (as described above), but also the second anchoring element to cam obliquely over the first anchoring element, forcing at least a portion of the second anchoring element into the bone hole wall.

In a further aspect of the invention, the second anchoring element comprises a substantially tubular element having a plurality of axially-oriented slots that define a plurality of flexible wall sections or wings. These wings are substantially aligned with the insertion stem (and with an axial channel of the second anchoring element) prior to deployment, but extend radially and obliquely outward into the wall of the bone hole as the second anchoring element is cammed over the first anchoring element.

In a further aspect of the invention, the first anchoring element is a substantially elongate, annular member, e.g., a "sleeve," having an outer surface for engagement with an inner surface of the bone hole. That outer surface may include one or more structures, protrusions, ridges and threads that facilitate such engagement.

In a further aspect of the invention, an insertion element as described above has a frangible portion at its proximal end that transfers a selected range of tensional forces through the stem, thus for example permitting it to be pulled through the first anchoring element. That frangible portion breaks away from the remainder of the stem upon application of still greater tensional forces, thus, detaching from the anchor, e.g., once the first anchoring element is fully deployed.

The insertion element may also have a head at the distal portion of the insertion stem. That head is adapted to stop movement of the insertion stem through the axial channel, i.e., once the proximal side of the head substantially abuts the distal end of the first anchoring element.

In still further aspects, the outer surface of the insertion stem may contain multiple projections, such as ribs or threads, to better engage the first or second anchoring elements.

In a further aspect of the invention, a suture retainer, such as a stat, groove, or aperture, is disposed on the distal portion of the insertion stem, preferably the head, such that a suture under tension will place the suture retainer in compression. Further, the insertion stem may contain an axially-oriented channel or groove to retain the suture.

In further aspects, the bone anchor assembly is comprised at least in part of biocompatible or bioabsorbable materials that are radiolucent or radio-opaque.

In further aspects, the invention provides methods for deploying a bone anchor assembly as described above, e.g, by placing the anchor in a predrilled bone hole, pulling on the insertion stem so as to move a large diametered (or larger cross-sectional) portion of the stem into a first anchoring element, and thereby expanding that element so that it is placed into compression fit within the hole. In embodiments incorporating a second anchoring element, the pulling step also results in the second anchoring element camming over the first so that the second element engages the bone hole walls.

Among the advantages of the invention are the ability to deliver the bone anchor with substantially no force on delivery. Thus, for example, unlike some prior art bone/suture anchors it is not necessary to exert a "downward" force on the anchor while its stem is being pulled "upwardly" through the bone hole. Further advantages of the invention are its ability to deliver a recessed bone anchor without the need for subsequently countersinking the anchor, e.g., with a hammer and punch. Moreover, the invention provides the ability to deliver the implanted bone anchor reliably to a specific depth in the bone hole with substantially no shifting of the anchor's position in the predrilled bone hole.

These and other aspects of the invention are evident in the drawings and in the description that follows.

DETAILED DESCRIPTION OF THE ILLUSTRATED EMBODIMENT

By way of overview, a bone anchor assembly according to the one embodiment of the invention has an annular anchoring sleeve that is slidably mounted on an insertion stem. A distal portion of the insertion stem has an outer diameter or cross-section that is greater than an inner diameter or cross-section of the sleeve. The assembly is placed in a bone hole and the insertion element is pulled proximally, while the sleeve is held in place by a deployment apparatus, thereby, causing the sleeve to expand radially into a pressure or compression fit with the bone hole.

In addition to the anchoring sleeve, the assembly can include a second anchoring element comprising a tubular member that is disposed on the insertion stem distal to the first anchor element. Slots at the proximal end of the second anchor form wings that normally rest parallel to the insertion stem. The inner diameter of the second anchor is a bit smaller than the outer diameter of the first anchor; hence, as the insertion member is pulled proximally, the wings cam over the distal end of the first anchor and into the walls of the bone hole.

A. The Insertion Stem and Expander Element

Figure 1A:
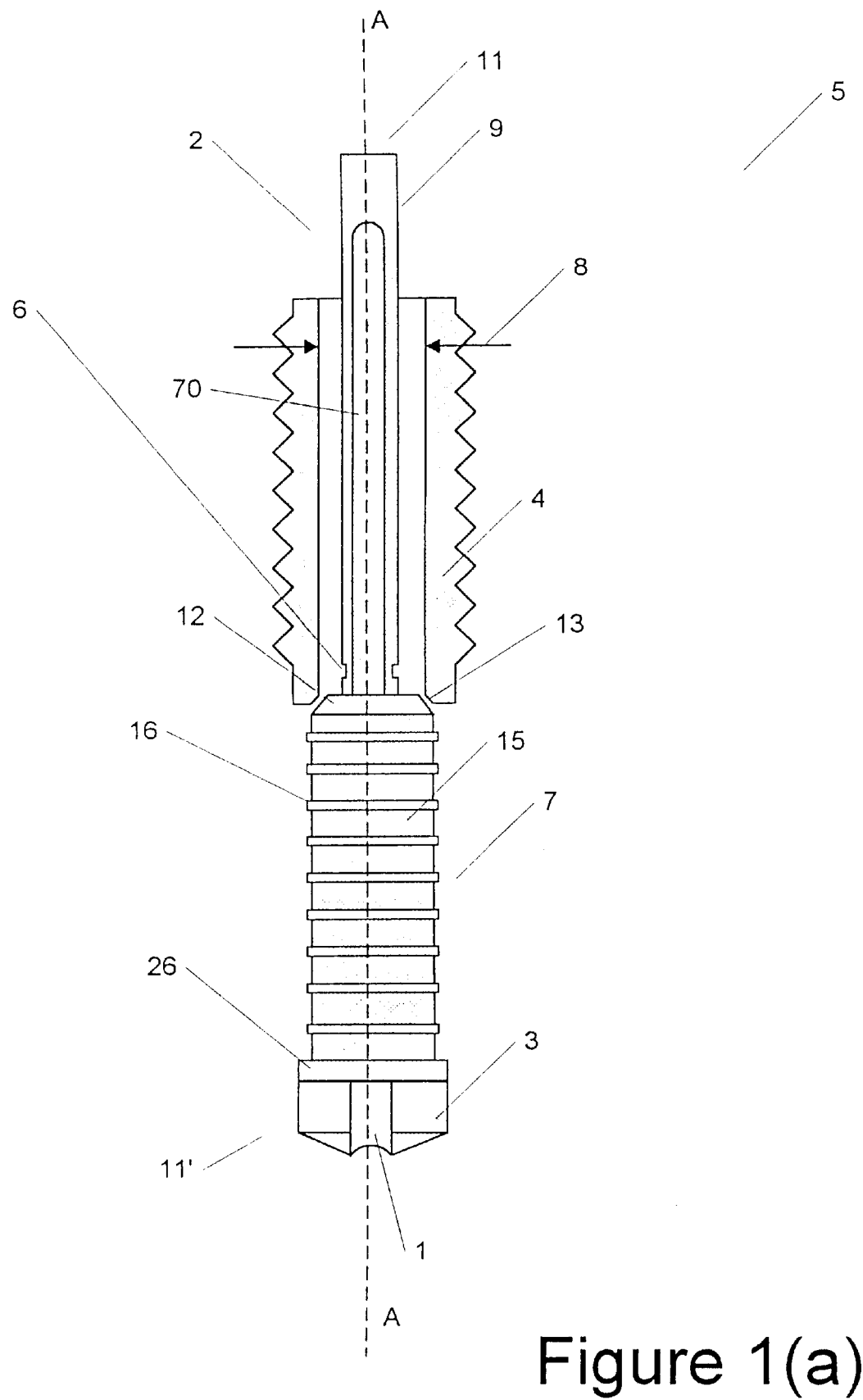
FIGS. 1(a)–1(b) depicts bone anchors according to a first preferred practices of the invention.

FIG. 1(a) shows a cross-section of a bone anchor assembly according to one embodiment of the invention. The assembly 5 includes an elongate insertion stem 2 having proximal 11 and distal 11' ends oriented along a longitudinal axis A—A. At the distal end of the stem 2 is a head 3, preferably, having an outer diameter larger than that of the remainder of the elongated stem 2. A slot 1 is preferably provided in the head 3 to retain a suture that is looped over the head. A slot 70 is also provided in the elongate body of stem 2 to route the suture along the length of the body and to prevent the suture from being crimped or torn during deployment. Though partially obscured by expander element 7, that slot runs from the head 3 to near the distal end 11' of the stem 2. In lieu of slot 1, the suture loop (or a suture end) can be retained in a hole, aperture or other structure in head 3, in another portion of the stem 2, or in the anchoring sleeve 4.

As shown in FIG. 1(a), the elongate portion of insertion stem 2 comprises portions of two differing diameters. The more proximal portion 9 of stem 2 has a diameter substantially equal to—and, preferably, smaller—than the inner diameter 8 of the anchoring sleeve. This permits the anchoring sleeve 4 to be slidably mounted on that portion of the stem 2. The more distal portion 7 has a diameter somewhat larger than the inner diameter 8 of anchoring sleeve 4. This portion 7 is pulled into the anchoring sleeve 4 in order to expand it into compression fit with the bone. Preferably, the junction of the larger-diametered portion 7 and the smaller-diametered portion 9 is tapered so as to create a camming surface 12, preferably, at an angle from 10° to 45° and, most preferably, at an angle of 30° relative to the longitudinal axis (A—A) of the insertion element. Tapered camming surface 12 corresponds to camming surface 13 of the anchoring sleeve 4.

The larger diametered portion 7 of stem 2 can have protrusions 16 on its outer surface. These protrusions may take the form of ribs, threads, a plurality of raised points or other shapes. In a preferred configuration of the type shown in FIG. 1(b), the larger diametered portion 7 (and, more particularly, the expander element 51) has a smooth outer surface.

The insertion stem 2 has a frangible portion 6 disposed proximal to larger diametered portion 7, preferably, near camming surface 12. The term "frangible" refers to a portion of elongated stem 2 that is breakable or frangible. In particular, FIG. 1(a) illustrates frangible portion 6 as a section of the elongated stem 2 having a thinner diameter than the remainder of the stem 2. The frangible section 6 is designed to break when sufficient tension is applied to it following deployment of the bone anchor assembly. The frangible portion may also take other forms such as a series of spokes, a plurality of attenuated membranes, or a material of lesser tensile strength.

Figure 1B:
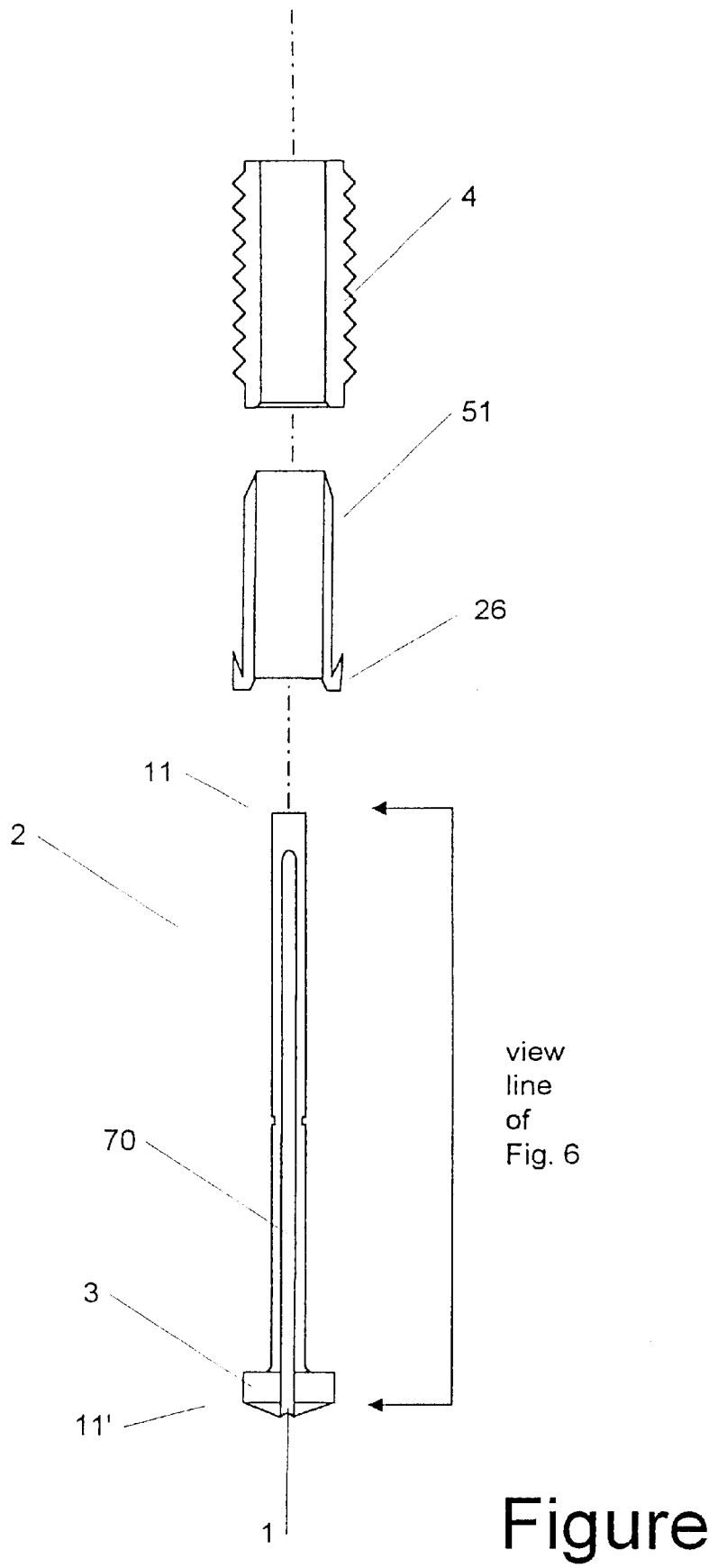

Though the insertion stem 2 can be formed as a single part, it is preferably comprises two parts. This is illustrated in FIG. 1(b), which shows that the larger diametered portion 7 of stem 2 is formed from a separate sleeve 51 slidably mounted on stem 2, proximal to head 3 and distal to anchoring sleeve 4. A flange 26 located at the distal end of expander element 51 prevents it from being pulled entirely through the anchoring sleeve during deployment. In the preferred, illustrated embodiment, the flange has a reverse taper as shown in the drawing. During deployment, the illustrated wings of flange 26 deform outwardly upon contact with the distal end of the anchoring sleeve further limiting the likelihood of "pull out."

As noted above, insertion stem 2 incorporates a suture retaining slot 1 that provides a track in stem 2 in which the suture (not shown) is slidingly engaged as it loops over head 3. This slot 1 prevents the suture from sliding off the head 3 during suture knot-tying or during and subsequent to emplacement of the anchor assembly in the bone. It will be appreciated that looping a suture over the head 3 provides added strength to the overall assembly.

Particularly, when the suture is under tension (e.g., during and subsequent to tying), the stem is in compression, as are head 3 and adjacent portions of stem. This configuration gives the suture retainer (and, therefore, the assembly as a whole) greater strength than found in configurations (such as where a suture-retaining aperture is disposed at the proximal end of insertion stem 2) in which the stem is placed under tension when the suture itself is under tension. Alternatives to the illustrated slot include placing an aperture (e.g., hole) through which the suture can be tied, or a shoulder around which the suture can be looped, at locations on anchoring element or insertion stem head 3 that are distal to the slot ends of the assembled suture anchor device.

With further reference to FIG. 1(b), a groove 70 extends from the slot 1 along stem 2 towards its proximal end. This serves to guide and protect the suture from being crimped by the anchor assembly during and subsequent to its emplacement in bone. The slot and track widths are sized in accord with the expected suture gauge. Preferably, the width is such that the suture can slide freely without excessive play. The slot and track depths are likewise determined by the expected suture gauge. Moreover it will be appreciated that, in the embodiment illustrated in FIG. 1(b), flange 26 and sleeve element 51 will be slidably mounted on stem 2 over the suture placed in groove 70.

An advantage of the two-piece pin construction shown in FIG. 1(b) is that the groove need not be incorporated into the expander element 51 itself. This permits the entire 360° circumference of element 51 to serve the expansion function, i.e., to force the anchoring sleeve 4 to expand as the element 51 is drawn into it. In embodiments where the groove 70 is incorporated into the element 51, those regions dedicated to the groove do not serve the expansion function as well.

Further embodiments of the invention incorporate refinements that facilitate fabrication of smaller suture anchoring assemblies. These refinements strengthen the assembly by reducing the stresses placed on its components of the assembly and, thereby, prevent failure of the anchoring assemblies during and subsequent to emplacement in the bone structures.

Figure 6:
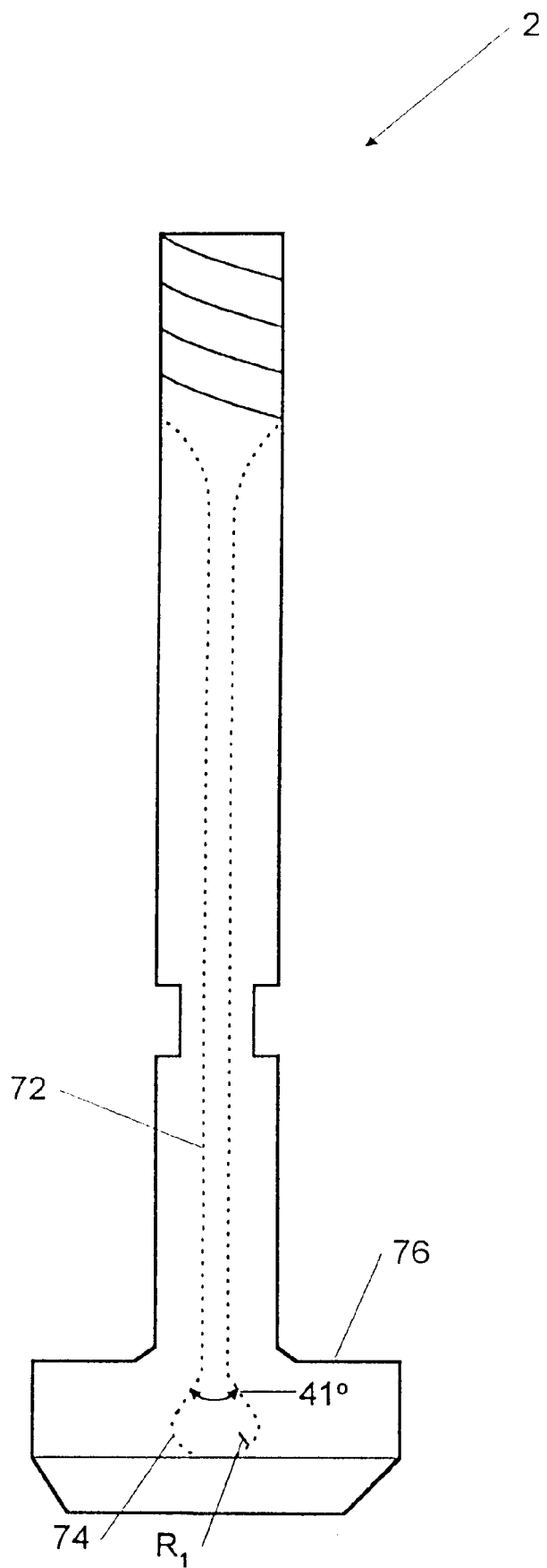
FIGS. 6–7 depicts further strength-enhancing modifications to insertion stems and second anchoring elements of bone anchors according to the invention.

FIG. 6 depicts a side cut-away view of insertion stem 2 and shows the shape of the support base (or floor) 72, at the base of the slot 1 and track 70, supporting the suture. As illustrated, the support base 72 runs longitudinally, parallel to the major axis of the stem 2 and ends in a tear drop shape 74 at the distal end of the stem, i.e., at slot 1, where the suture loops over head 3. In addition to a tear drop shape, the support base 72 can have other shapes, preferably, ones in which the base has a cross-section at the distal end that is larger than that at the proximal end.

The tear drop (or other such) shape is advantageous over a conventional rectilinear shape insofar as the tear drop distributes over a greater surface area the compressional load applied to the head 3 by the suture, e.g., intra and post operatively. As shown in the drawing, the tear drop opens at an angle of 30°–60° and, more preferably, of 41° beginning a point distal to the proximal side 76 of the head. As further illustrated the "corners" of the tear drop 74 define a radius $R_1$ of 0.001–0.020 inches and, preferably, 0.010 inches for a #2 suture. Proportionally sized radii can be selected for where the expected suture gauge differs from this.

Referring back to FIG. 1(b), the stem 2 incorporates a chamfer at the junction of the elongate portion of the stem and head 3. The chamfer, which is angled at 20°–70° and, more preferably, 45°, also serves to reduce the concentration of tensional stress on head 3 during and subsequent to emplacement of the anchor assembly in bone.

A used herein, the term "chamfer" refers to conventional straight-edge chamfers, as well as blend radii.

B. The First Anchoring Element

Figure 2:
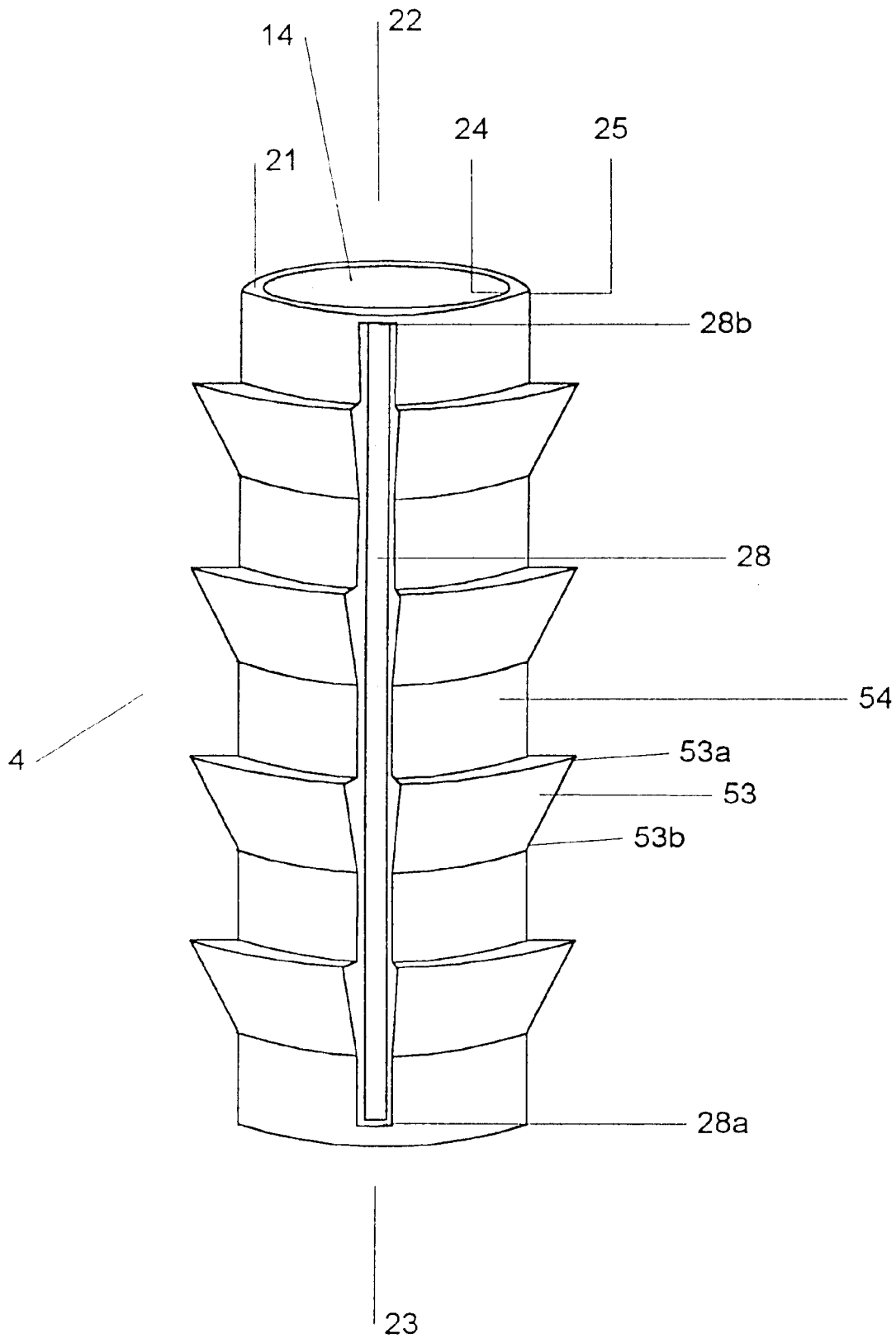
FIG. 2 depicts a first anchoring element for use with the bone anchor of FIGS. 1(a)–1(b)

Referring to FIG. 2, the first anchoring element 4, otherwise known herein as a "sleeve" or "anchoring sleeve," comprises a substantially tubular element having distal 23 and proximal 22 ends connected by way of an axial channel 14 extending from distal end 23 to the proximal end 22. Element 4 has inner 24 and outer 25 peripheral surfaces forming a wall 21. The element 4 also has an inner diameter $d_i$ and an outer diameter $d_o$ that are defined transversely with respect to the axis of axial channel 14. A cross-section of inner axial channel 14 of the anchoring sleeve may be circular, or of any other cross-sectional shape.

In one embodiment of the invention, the outer peripheral surface of first anchoring element 4 has protrusions 53 that may take the form of ribs, threads, a plurality of raised points or other shapes. In a preferred embodiment, protrusions 53 are ridges having walls angled such that each ridge, as viewed from a cross-section transverse to the axis of first anchoring element 4, has a smaller cross-section at the distal end 53b of the ridge than at the proximal end 53a. This preferred ridge acts to increase the holding power of the anchor. Other configurations of protrusions 53 may of course be used to facilitate holding the anchor in place. Indeed, no protrusions may be necessary where the surface-to-surface frictional forces of the anchoring element and stem are great enough.

In embodiments of the invention in which the first anchoring element 4 is comprised of bioabsorbable and other less flexible materials, one or more of axially-oriented slots 28 are defined in the wall 21 in communication with the axial channel 14. These slots may extend along the entire length of the wall 21 or, as shown in the drawing, from points 28a, 28b intermediate to the proximal and distal ends 22, 23. In alternate such embodiments, these slots 28 do not communicate with the axial channel but are covered by a thin, frangible surface (not shown) such as, for example, a membrane or a series of spokes. In a preferred bioabsorbable anchor comprising a 0.2 inches long sleeve of polylactic acid, the slots 28 run the entire length of the element 4, have a width of 0.015 inches and extend through the entire wall of the sleeve.

As shown in FIG. 1(a), the anchoring sleeve 4 has an inner diameter that is substantially equal to, or larger than, the outer diameter of portion 9 of the insertion stem. Accordingly, in its non-expanded state, the anchoring sleeve 4 is slidably mounted on insertion stem portion 9. Inner diameter 8, however, is preferably smaller than the outer diameter of portion 7 of stem 2. Accordingly, when that portion 7 of the stem is drawn into the anchoring sleeve 4, it causes its walls to expand outward and into the bone wall.

Figure 3A:
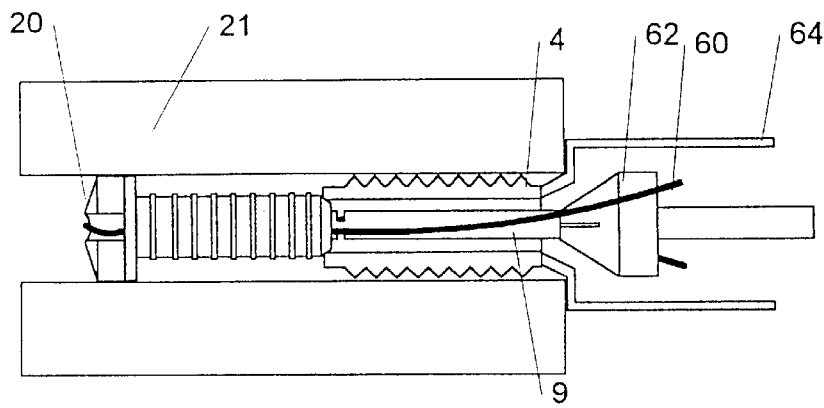
FIGS. 3(a)–3(c) depict the deployment of the anchor of FIG. 1 in a predrilled bone hole.
Figure 3B:
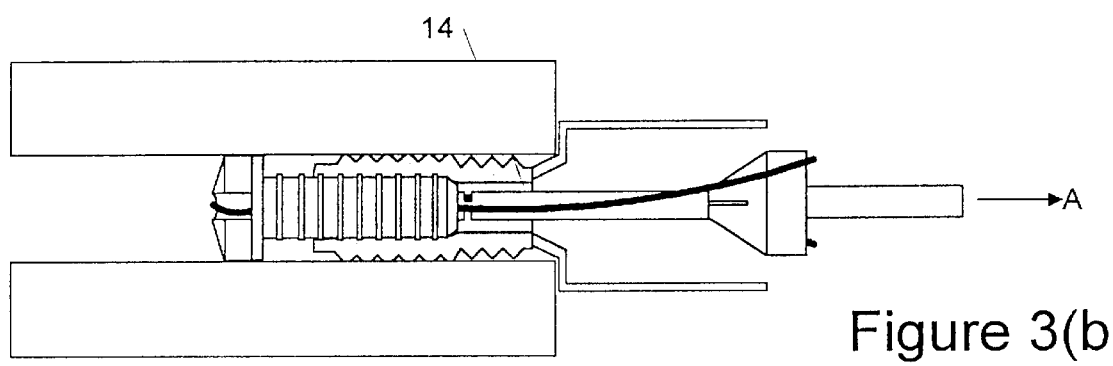
Figure 3C:
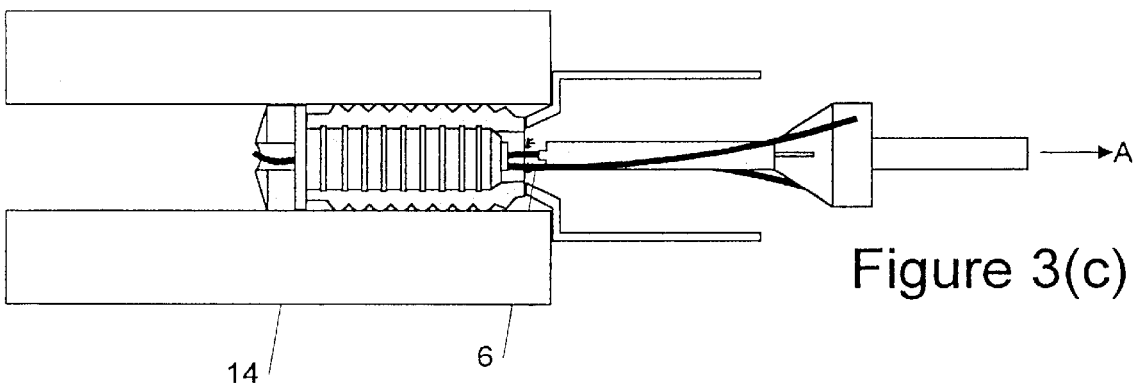

The insertion stem of the anchor may have at the proximal end of stem 2 a portion, e.g., containing protrusions, ribs or threads, suitable for engaging a deployment device. Referring to FIGS. 3(a)–3(c), a collet 62 of a stem-pulling portion of that deployment device grasps the insertion element at its proximal end of stem 2, while sleeve-holding portion 64 of the deployment is in contact with the proximal portion of the first anchoring element.

These two portions 62, 64 of the deployment device are moved relative to one another in order to move the insertion stem 2 proximally within the first anchoring element 4. More particularly, the colleted stem-pulling portion 62 is pulled in direction A, while the sleeve-holding portion prevents movement of at least the proximal end of the sleeve 4.

An advantage of this manner of deployment is that (i) the pulling force exerted by portion 62 is translated entirely into radial expansion of the sleeve 4 for compression fit with the bone hole, and (ii) the surgeon need not exert a downward (or pushing) force on the deployment device in order to keep the sleeve in place during deployment (put another way, the deployment device is coupled to the first anchoring element such that a pulling force exerted on the insertion stem in order to move it proximally in the axial channel is translated substantially into radial expansion of the first anchoring element). These advantages are in contradistinction to prior art anchors—particularly, those in which an expansion member (e.g., analogous to an insertion stem) is pushed into an expandable member (e.g., analogous to a sleeve)—wherein the expansion member's movement can cause longitudinal extension of the expandable member and wherein it is necessary for the surgeon to exert a downward force in order to insure that the expandable member remains in the bone hole during deployment.

Such advantageous deployment may be realized by use of a hand-actuated, pistol-type deployment device of the type illustrated in PCT/US95/14724, filed Nov. 9, 1995, claiming priority of US 08/337,944, filed Nov. 10, 1994, the teachings of both of which are incorporated herein by reference. Such a device consists of two handle elements slidably engaged to provide a comfortable pistol grip by which one handle element can be moved in a proximal-distal direction with respect to the other handle element by squeezing the pistol grip. One of the handle element is coupled to the sleeve 4 (e.g., via contact of the distal end of the housing of the device with the proximal end of the sleeve), while the other handle is coupled to the insertion stem. By squeezing the pistol grip, the insertion stem 2 to be pulled through the sleeve 4, while the latter remains within the bone hole.

FIGS. 3(a) through (c) illustrate deployment of the bone anchor assembly 5 of FIG. 1(a). In each FIGS. 3(a)–(c), a suture 60 is shown as being looped over slot 1 in stem head 3. The trailing ends of suture 60 exit the bone hole where they are available to the surgeon. Particularly, FIG. 3(a) illustrates the anchoring sleeve 4 slidably mounted on the insertion element 2 prior to deployment. The sleeve 4 is disposed such that its proximal end is slightly recessed within a predrilled hole 20 in bone 21.

FIG. 3(b) illustrates the insertion element 2 being pulled into the axial bore 14 of anchoring sleeve 4. Tension is applied to stem 9 of insertion element 2 (in the direction shown by arrow A) by the colleted stem-pulling portion of the deployment device, while the anchoring sleeve is held substantially immobile within bone hole by the sleeve-holding portion of that device. These forces act to move the insertion element in the direction of arrow A such that larger diametered portion 7 of insertion element is pulled into the axial channel 14 of anchoring sleeve 4. As a result, the wall of anchoring sleeve 4 expands outwardly and into the walls of the bone hole 20.

As shown in FIG. 3(c), the insertion stem—and, significantly, the larger diametered portion 7—is pulled proximally through the axial bore 14, until further motion is retained by abutment of flange 26 with the distal end 23 of anchoring sleeve 4. At this point, the deployment device continues to exert tension on the stem 9, causing the frangible portion 6 to shear. This facilitates removal of the excess portion of stem 9 and, likewise, disengages the deployment device. Preferably the frangible portion 6 of insertion stem 9 is disposed so that, when the stem is broken at its frangible portion 6, the remaining stub of the insertion element 2 does not extend above the surface of the bone. Alternatively, in a sutureless design, the remaining stub can protrude above the bone, e.g., for attachment of a washer.

C. The Second Anchoring Element

Figure 4A:
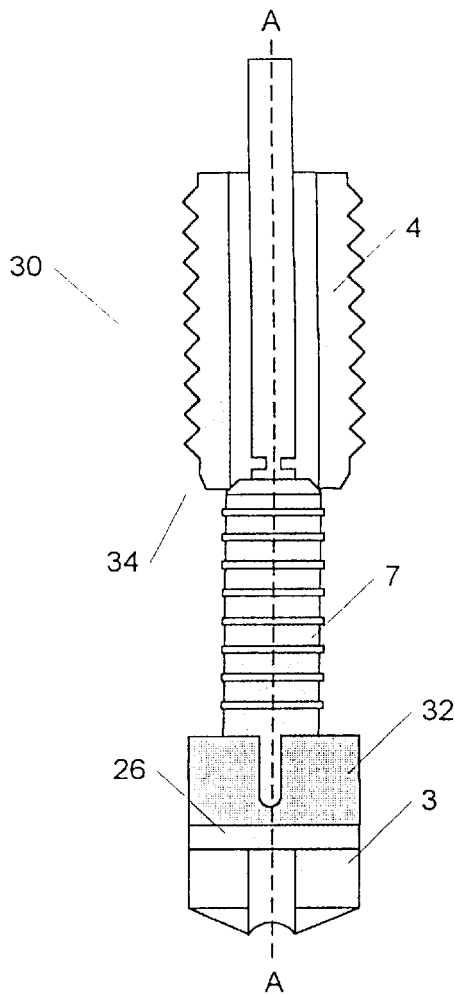
FIGS. 4(a) and 4(b) depict a bone anchor according to a second preferred practice of the invention.

FIG. 4(a) depicts an alternate embodiment of a bone anchor assembly according to the invention. The assembly 30 is constructed and operated similarly to bone anchor 5 of FIG. 1(a), except insofar as it includes a second anchoring element 32 mounted on insertion stem 2 between stem head 3 and first anchoring element 4.

Figure 4B:
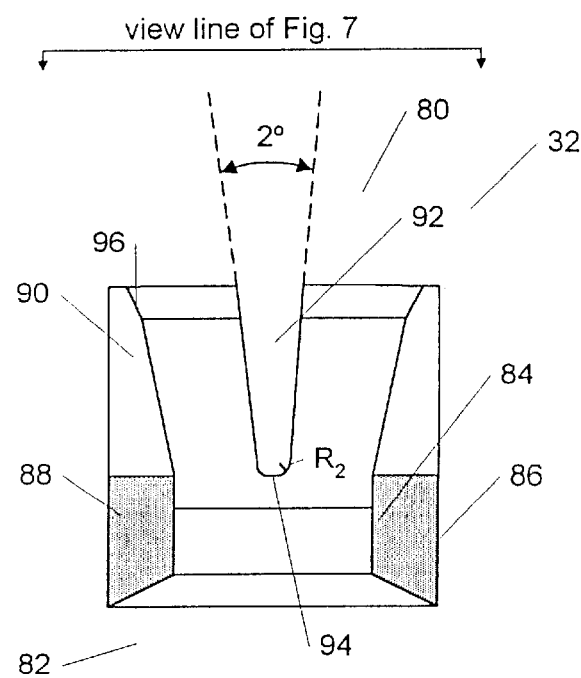

Referring to FIG. 4(b), the second anchoring element 32 is substantially tubular, having opposed proximal 80 and distal 82 ends connected by way of a central axial channel (not labeled) extending therebetween. Distal end 82 is engaged with flange 26 of insertion stem 2, as shown in FIG. 4(a). Second anchoring element 32 has inner 84 and outer 86 peripheral surfaces forming a wall 88. Defined in the wall, and in communication with axial channel, are a series of axially-oriented slots 92 that begin at the proximal end 80 and extend some distance towards the distal end 94. Each of the series of axially-oriented slots 92 in second anchoring element 32 define a flexible wall section or wing 90 located between each slot. The second anchoring element 32 can include a plurality of slots 92 and, thereby, a corresponding number of wall sections 90. Although the number of slots (and wall sections) can range from 2 to 10 (or upwards), a preferred number of slots (and wall sections) is three or four.

As shown in FIG. 4(b), each wall section 90 tapers gradually from a base portion 88 to the proximal end 22. That taper can be, for example, 0° to 20° degrees and, preferably, is about 8°. Camming surfaces 96 at the tips of the walls have more pronounced tapers. These can range, e.g., from 30° to 75° and is, preferably, about 60°.

Each wall section or wing 90 is more flexible at its respective proximal end, in part because the wing 90 is defined between slots that extend directly from the proximal end 80 of the anchoring element. The distal ends of the respective wings 90 are co-extensive with the distal end 82 of anchoring element 32. The proximal ends of the wings, i.e., the wing tips, are flexible and free to be forced radially outwardly during deployment. In an alternative embodiment, axially oriented slots 92 are not in complete communication with axial channel (not shown) but are covered with a thin, frangible membrane or frangible partial membranes that are capable of breaking upon impact thereby allowing the wings to expand radially outward.

In a preferred embodiment, the proximal, free ends of the wings 90 comprise a tapered or beveled camming surface 96, the taper ranging from about 10 degrees to about 60 degrees relative to longitudinal axis A—A. Most preferably the tapered camming surfaces 96 of wings 90 are at an angle of about 45 degrees relative to longitudinal axis A—A. Camming surfaces 34 on the distal end of the anchoring sleeve 4 can be chamfered or tapered at an angle complimentary to that of the camming surfaces 96.

Figure 7:
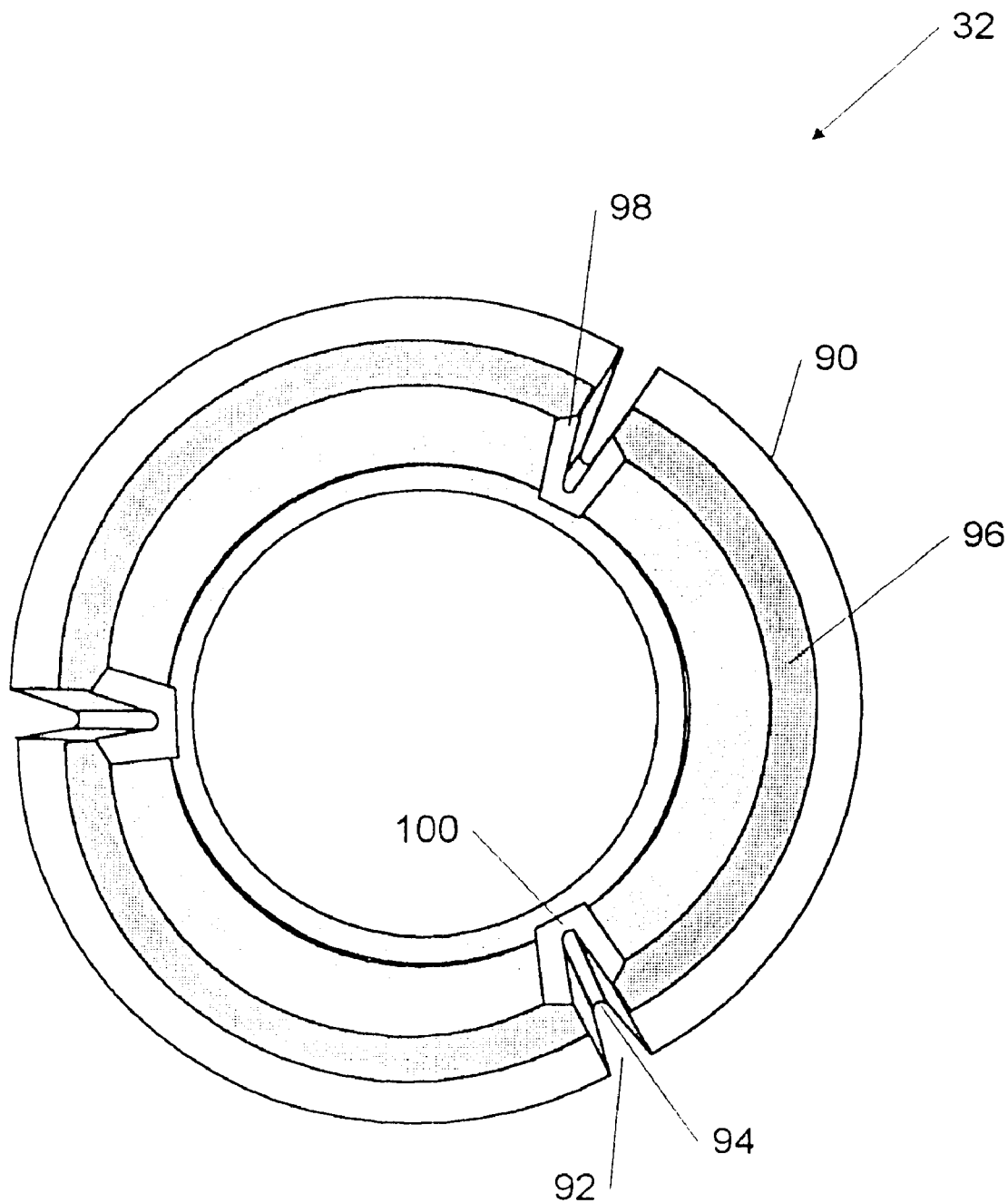

In order to withstand the stresses placed on the walls 90 and slot bases 94 of the suture anchoring assembly and, especially, smaller suture anchoring assemblies, the second anchoring element 32 incorporates a number of features to distribute the stresses of emplacement. This gives smaller assemblies, which may be constructed from polymers and copolymers (as described above), greater holding strength without risk of failure. As shown in FIGS. 7 and 8, stress distribution is accomplished by rounding, or chamfering, stress-bearing edges of the walls 90 and slots bases 94, as well as by tapering the walls, in order to distribute applied loads.

For example, as shown in FIG. 4(b), the distal ends 94 of the slots of anchoring element 220 are rounded. This reduces stress on, and thereby prevents failure of, the second anchoring element 32 in the region adjacent to those rounded distal ends. As illustrated, the rounded ends of the slots 92 define radii $R_2$ of 0.001–0.020 in and, preferably, 0.010 in for a three-wing or four-wing polymer anchor having an outside diameter of 3.5 mm, an inside diameter of 2 mm, an overall length of 5.5 mm, and a wing length of 3 mm. Proportionally sized radii can be selected for anchoring elements whose dimensions differ from this.

As further shown in FIG. 4(b), the slots 92 are tapered. Particularly, they are wider at the proximal end then at the distal end. The degree of taper may vary from 0°–10° and, preferably, is about 2°. This taper also reduces the stress on, and thereby prevents failure of, the anchoring element 220 in the region adjacent to the distal ends of the slots 92.

FIG. 7 is a top view of a preferred anchoring element 32 according to the invention. As shown in the drawing, the edges of wall sections 90 are chamfered to reduce stress during and subsequent to emplacement of the assembly in bone. More particularly, each wall section 90 is chamfered along its inner-top edge 96, and radiused along the edges of the slot 92 that defines its inner-side edges 98, as shown. The chamfer along the inner-top edge 96 can be substituted with a blend radius.

For a like-sized anchoring element, the inner-side edges 98 have a blend radius of, e.g., of 0.001–0.020 inches and, preferably, 0.010 inches for a three-wing or four-wing anchor having dimensions as specified above. Again, proportionally sized radii can be selected for anchoring elements whose dimensions differ from this. This radius continues along the entire inside edge of each slot 92, including the inside edge 100 at the bottom 94 of each slot.

Prior to deployment, the wing portions 90 lie substantially parallel to the longitudinal axis A—A of insertion element 2, as shown in FIGS. 4(a) and 4(b). During deployment, the forces exerted by the colleted stem-pulling portion of the deployment device pull the larger diametered portion 7 of insertion element into the axial channel 14 of the substantially immobile anchoring sleeve 4, causing the sleeve 4 to expand outwardly and into the walls of the bone hole 20 At the same time, the wings 90 of the second anchoring element cam over the tapered camming surfaces 34 at the distal end of the sleeve, forcing those wings radially outwardly into the walls of the bone hole.

Figure 5A:
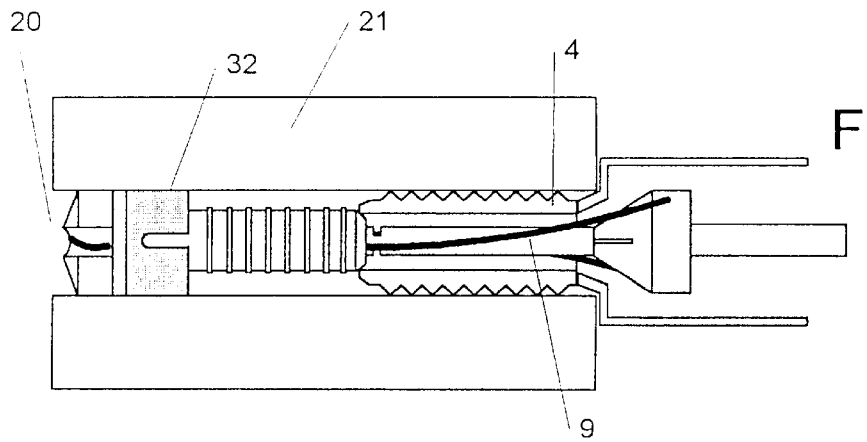
FIGS. 5(a)–5(c) depict the deployment of the anchor of FIG. 4(a) in a predrilled bone hole.
Figure 5B:
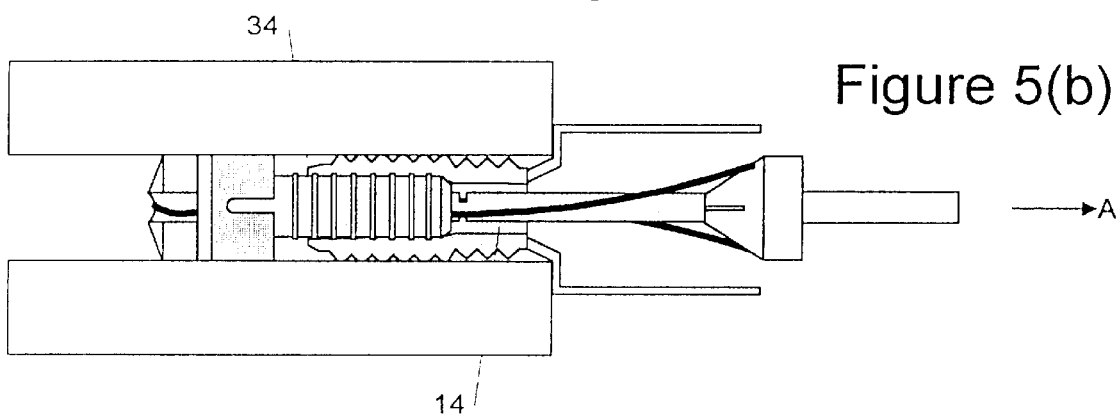
Figure 5C:
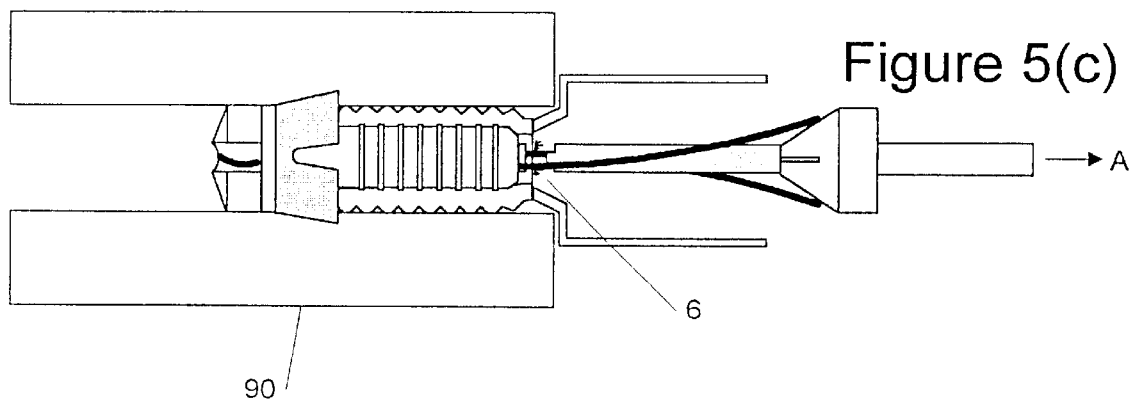

Such deployment is illustrated in FIGS. 5(a)–(c), which parallel the actions shown in FIGS. 3(a)–(c), discussed above, except insofar as the effects of deployment on the second anchoring element 32. Particularly, referring to FIG. 5(a), it is seen that prior to deployment (but after the anchor assembly is inserted in the bone hole 20), the wings of element 32 lie substantially parallel to the longitudinal axis of the insertion element 2. As deployment continues in FIG. 5(b), the wings remain in this configuration until their proximal ends abut and begin to cam over camming surface 34 of the first anchoring element. This is shown in FIG. 5(c), where it is seen that as the wings of the second anchoring element cam over the first anchoring element, the tips of the wings are driven into the walls of the bone hole.

D. Materials

Component parts of the bone anchor assembly may be fabricated by conventional molding or extrusion procedures. The component parts are preferably constructed of biocompatible material. The term "biocompatible" means that the anchoring element material is chemically and biologically inert. Suitable materials for the anchoring element include, for example, an implant grade high density polyethylene, low density polyethylene (PE); acetal and polypropylene. Of these, Polysulfone P-1700 has been FDA listed as a class 6 material.

The anchoring element may also be bioabsorbable. The term "bioabsorbable" refers to those materials that are meant to be decomposed or degraded by bodily fluids via hydrolysis, such as, for example, blood and lymph. The anchoring element is preferably made from a biodegradable polymer or copolymer of a type selected in accordance with the desired degradation time. That time in turn depends upon the anticipated healing time of the tissue which is the subject of the surgical procedure. Known bioabsorbable polymers and copolymers range in degradation time from about 3 months for polyglycolide to about 48 months for polyglutamic-co-leucine. A common bioabsorbable polymer used in absorbable sutures is poly (L-lactide) which has a degradation time of about 12 to 18 months.

The following Table set forth below lists polymers which are useful for the bioabsorbable material employed for the anchoring element, and other parts of the bone fastener as described below. These polymers are all biodegradable into water-soluble, nontoxic materials which can be eliminated by the body.

TABLE

| | |
|---|---|
| Polycaprolactone | Poly (L-lactide) |
| Poly (DL-lactide) | Polyglycolide |
| 95:5 Poly (DL-lactide-co-glycolide) | Polydioxanone |
| Polyesteramides | |
| Copolyoxalates | |
| Polycarbonates | |
| Poly (glutamic-co-leucine) | |
| 90:10 Poly (DL-lactide-co-glycolide) | |
| 85:15 Poly (DL-lactide-co-glycolide) | |
| 75:25 Poly (DL-lactide-co-glycolide) | |
| 50:50 Poly (DL-lactide-co-glycolide) | |
| 90:10 Poly (DL-lactide-co-caprolactone) | |
| 75:25 Poly (DL-lactide-co-caprolactone) | |
| 50:50 Poly (DL-lactide-co-caprolactone) | |

E. Conclusion

A further appreciation of preferred suture anchor assemblies according to the invention may be attained by reference to the three-dimensional drawings and schematics filed in the Appendix herewith. It should be understood that various changes and modifications of the preferred embodiments may be made within the scope of the invention. Thus, for example, it will be appreciated that, while the illustrated embodiments are constructed of polymers, copolymers, and bioabsorbable materials, they can also be constructed of metals and other biocompatible materials. Thus it is intended that all matter contained in the above description be interpreted in an illustrative and not limited sense.

In view of the forgoing, what we claim is:

1. An anchor for coupling an object to bone comprising:

a first anchoring element for insertion into a hole in the bone, the first anchoring member including an axial channel extending between proximal end and distal ends thereof, the first anchoring element being slidably mounted on an insertion stem, the insertion stem including a portion having a greater outer diameter than an inner diameter of the axial channel, that portion being referred to herein as the portion of greater diameter, the insertion stem being adapted to move proximally in the axial channel to cause the portion of greater diameter to move at least partially through that channel and, thereby, to cause the first anchoring element to expand into a pressure fit with the bone hole, a second anchoring element disposed on the insertion stem distal to the portion of greater diameter, the first and second anchoring elements being arranged so that proximal movement of the insertion stem causes the second anchoring element to cam over the first anchoring element, forcing at least a portion of the second anchoring element into a wall of the bone hole.

2. The anchor of claim 1, wherein the second anchoring element has a channel therethrough for passage of the insertion stem, on which the anchoring element is disposed.

3. The anchor of claim 2, wherein the second anchoring element comprises a wall defined by an inner surface of the channel of the second anchoring element and by outer surface of the second anchoring element, the wall having a plurality of axially-oriented slot, beginning at a proximal end of the second anchoring element and extending toward the distal end, the slots defining a plurality of flexible wall sections.

4. The anchor of claim 3, wherein the flexible wall sections are substantially aligned with the channel of the second anchoring element prior to proximal movement of the second anchoring element.

5. The anchor of claim 4, wherein proximal movement of the second anchoring element causes the flexible wall sections to cam over the first anchoring element and to expand obliquely outwardly into the wall of the bone hole.

6. The anchor of claim 3, wherein an inner diameter of at least a portion of the channel of the second anchoring element is smaller than the outer diameter of at least a portion of the first anchoring element.

7. An anchor of claim 1, wherein the first anchoring element is a substantially elongate, annular member having an outer surface for engagement with an inner surface of the bone hole.

8. An anchor of claim 7, wherein the outer surface of the first anchoring element includes structure for engagement with the inner surface of the bone hole.

9. An anchor of claim 8, wherein the structure on the outer surface of the first anchoring element comprises any of a protrusion, ridge and thread.

10. The anchor of claim 1, wherein a proximal end of the insertion stem has an outer diameter that is lesser or not substantially greater than an inner diameter of the axial channel, and wherein a distal end of the insertion stem comprises the portion of greater diameter.

11. The anchor of claim 10, wherein the insertion stem includes a frangible portion at a proximal end thereof.

12. The anchor of claim 11, wherein the frangible portion is adapted to detach on application of a selected force thereto.

13. The anchor of claim 12, wherein the frangible portion is adapted to transfer a proximally-directed force through the insertion stem to cause the portion of greater diameter to move proximally in the axial channel, prior to detaching.

14. The anchor of claim 13, wherein the insertion stem comprises a head distal to the portion of greater diameter.

15. The anchor of claim 14, wherein the head is adapted to stop movement of the insertion stem in the axial channel, once the head is in substantial abutment with a distal end of the first anchoring element.

16. A method of anchoring an object to bone, comprising placing the anchor of claim 13 in a bone hole, the anchor being placed in the hole distal end first, applying a proximally-directed force to the frangible portion of the insertion stem to move it proximally with respect to the first anchoring element to cause the portion of greater diameter to move at least partially through the axial channel and, thereby, to cause the first anchoring element to expand into a pressure fit with the bone hole, continuing application of the proximally-directed force to the frangible portion after the portion of greater diameter has moved at least partially through the axial channel to cause the frangible portion to detach.

17. A method of claim 16, wherein the proximally-directed force is applied to the frangible portion after the portion of greater diameter has moved at least partially through the axial channel so as to cause the frangible portion to detach substantially at or below a surface of the bone.

18. The anchor of claim 1, comprising a suture retainer disposed on the insertion stem for coupling a suture to the anchor.

19. The anchor of claim 18, wherein the suture retainer is disposed such that a suture disposed therein under tension places the suture retainer in compression.

20. The anchor of claim 19, wherein the suture retainer is disposed at a distal end of the insertion stem.

21. The anchor of claim 20, wherein the suture retainer comprises any of a slot, groove and aperture.

22. The anchor of claim 19, wherein the suture retainer is disposed on the head.

23. The anchor of claim 22, wherein the suture retainer comprises any of a slot, groove and aperture.

24. The anchor of claim 1, wherein said insertion stem includes a channel for engagement with a suture.

25. The anchor of claim 1, wherein an outer surface of the insertion stem element has defined thereon a plurality of projections on the portion of greater diameter for engagement with the axial channel.

26. A method of anchoring an object to bone, comprising:

placing the anchor of claim 1 in a bone hole, the anchor being placed in the hole distal end first, moving the insertion stem proximally with respect to the first anchoring element (i) to cause the portion of greater diameter to move at least partially through the axial channel and, thereby, to cause the first anchoring element to expand into a pressure fit with the bone hole, and (ii) to cause the a second anchoring element to cam over the first anchoring element, forcing at least a portion of the second anchoring element into a wall of the bone hole.

27. The method of claim 26, comprising the step of holding the first anchoring element substantially in place while moving the insertion stem proximally.

28. The method of claim 27, wherein the holding step comprises holding the first anchoring element by a proximal end thereof.

29. The method of claim 26, wherein the moving step comprises pulling the insertion stem out of the bone hole while holding the first anchoring element substantially in place in the bone hole.

30. A system for coupling an object to bone, comprising an anchor that includes
   A. an insertion stem,
   B. a first anchoring element for insertion into a hole in the bone, the first anchoring element being substantially elongate and having an outer surface for engagement with an inner surface of the bone hole, the first anchoring element including an axial channel extending between the proximal and distal ends thereof, the first anchoring element being disposed on the insertion stem,
   C. an expander element disposed on the insertion stem distal to the first anchoring element and having an outer diameter greater than an inner diameter of at least a portion of the axial channel,
   D. the expander element and the first anchoring element being arranged so that proximal movement of the insertion stem in the bone hole causes the expander element to move at least partially through the channel, thereby, causing the first anchoring element to expand into a pressure fit with the bone hole,
   E. wherein the anchor includes a second anchoring element disposed on the insertion stem distal to the expander element, the first and second anchoring elements being arranged so that proximal movement of insertion stem causes the second anchoring element to cam over the first anchoring element, forcing at least a portion of the second anchoring element into a wall of the bone hole.

31. The system of claim 30, wherein the deployment mechanism is in at least contact with the proximal end of the first anchoring element so as to restrict movement of at least that end of the first anchoring element while the insertion stem is moving proximally in the axial channel.

32. The system of claim 31, wherein a pulling force exerted by the deployment mechanism on the insertion stem is translated substantially into radial expansion of the first anchoring element.

33. The system of claim 30, wherein the deployment mechanism is at least in contact with the first anchoring element such that the deployment mechanism places substantially equal and opposite forces on that anchoring element while the insertion stem moves proximally therethrough, thereby, placing substantially no net force on the deployment device.

34. The system of claim 30, wherein the expander element has a reverse taper on an outer surface at a distal end thereof, said reverse taper inhibiting movement of that distal end through the axial channel.

35. The system of claim 34, wherein the insertion stem includes a frangible portion at a proximal end thereof.

36. The system of claim 35, wherein the frangible portion is adapted to detach on application of a selected force to the insertion stem by the deployment mechanism.

37. An anchor for coupling an object to bone comprising:

a first anchoring element for insertion into a hole in the bone, the first anchoring element including an axial channel extending between proximal and distal ends thereof, the first anchoring element being slidably mounted on an insertion stem, the first anchoring element having a wall defined by an inner surface of the axial channel and an outer surface of the first anchoring element, the wall having at least one slot therein extending at least partially therethrough, the insertion stem including a portion having a greater outer diameter than an inner diameter of the axial channel, that portion being referred to herein as the portion of greater diameter, the insertion stem being adapted to move proximally in the axial channel to cause the portion of greater diameter to move at least partially through that channel and, thereby to cause the first anchoring element to expand into a pressure fit with the bone hole, a second anchoring element disposed on the insertion stem distal to the portion of greater diameter, the first and second anchoring elements being arranged so that proximal movement of the second anchoring element within the bone hole causes the second anchoring element to cam over the first anchoring element, forcing at least a portion of the second anchoring element into a wall of the bone hole.

38. The anchor of claim 37, wherein at least one of the first anchoring element, the second anchoring element and the insertion stem comprises a bioabsorbable material.

* * * * *